| United States Patent [19] | [11] Patent Number: 4,753,939 |
|---|---|
| DeGraw, Jr. et al. | [45] Date of Patent: Jun. 28, 1988 |

[54] PROCESS AND COMPOSITION FOR TREATMENT OF LUEKEMIA AND PROCESS FOR PREPARING THE SAME

[75] Inventors: Joseph I. DeGraw, Jr., Sunnyvale, Calif.; Francis M. Sirotnak, New York, N.Y.

[73] Assignees: SRI International, Menlo Park, Calif.; Sloan Kettering Institute for Cancer Research, New York, N.Y.

[21] Appl. No.: 871,208

[22] Filed: Jun. 5, 1986

Related U.S. Application Data

[63] Continuation of Ser. No. 808,579, Dec. 13, 1985, abandoned, which is a continuation of Ser. No. 754,370, Jul. 11, 1985, abandoned, which is a continuation of Ser. No. 701,885, Feb. 15, 1985, abandoned, which is a continuation of Ser. No. 645,387, Aug. 29, 1984, abandoned, which is a continuation of Ser. No. 513,254, Jul. 12, 1983, abandoned, which is a continuation of Ser. No. 397,274, Jul. 12, 1982, abandoned, which is a continuation of Ser. No. 75,913, Sep. 17, 1979, Pat. No. 4,393,064, and a continuation-in-part of Ser. No. 883,627, Mar. 6, 1978, abandoned, and Ser. No. 761,152, Jan. 21, 1977, abandoned, and Ser. No. 664,213, Mar. 5, 1976, abandoned.

[51] Int. Cl.$^4$ .................. A61K 31/50; A61K 31/495
[52] U.S. Cl. .................................................. 514/249
[58] Field of Search ........................................ 514/249

[56] References Cited

PUBLICATIONS

Degraw et al., J. of Med. Chem., 1974, vol. 17, No. I, pp. 552–553.

Primary Examiner—Jerome D. Goldberg

[57] ABSTRACT

A process and composition are provided employing 10-ethyl- 10 deazaminopterin for treating leukemia, as well as other tumor systems including of ascitic character.

18 Claims, No Drawings

PROCESS AND COMPOSITION FOR TREATMENT OF LUEKEMIA AND PROCESS FOR PREPARING THE SAME

ORIGIN OF INVENTION

The invention described herein was in part made in the course of work under a grant or award from the National Institute of Health, Department of Health, Education and Welfare.

This is a continuation of application Ser. No. 808,579, filed Dec. 13, 1985, now abandoned, which in turn is a continuation of Ser. No. 754,370, filed July 11, 1985, now abandoned, which in turn is a continuation of Ser. No. 701,885, filed Feb. 15, 1985, now abandoned, which in turn is a continuation of Ser. No. 645,387, filed Aug. 29, 1984, now abandoned, which in turn is a continuation of Ser. No. 513,254, filed July 12, 1983, now abandoned, which in turn is a continuation of Ser. No. 397,274, filed July 12, 1982, now abandoned, which in turn is a continuation of Ser. No. 75,913, filed Sept. 17, 1979, now U.S. Pat. No. 4,393,064, patented July 12, 1983, which in turn is a continuation-in-part of Ser. No. 883,627, filed Mar. 6, 1978, of Ser. No. 761,152, filed Jan. 21, 1977, and of Ser. No. 664,213, filed Mar. 5, 1976, all three now abandoned.

Leukemia is an acute or chronic disease of unknown cause in man and other warm-blooded animals. It is characterized by an abnormal increase in the number of immature leukocytes in the tissues of the body and in the circulating blood. The disease apparently affects the blood-forming organs, and is classified according to the type of leukocyte that is being proliferated abnormally. The disease is one of a number of forms of neoplastic disease, and the development of drugs for amelioration or curing the disease has occupied the attention of research organizations for many years, and until most recently without appreciable success. Today, many forms of leukemia can be effectively treated with drugs. In the case of combination chemotherapy with acute lymphocytic leukemia in children a large percentage (50–60%) of five year survivals are obtained, and the disease is now classified as curable.

In accordance with the invention, it has been determined that leukemia, as well as other malignancies, including ascitic tumors, can be ameliorated in warm-blooded lower animals and humans by the administration of 10-ethyl-10-deazaminopterin.

The 10-ethyl-10-deazaminopterin of the invention has the structure:

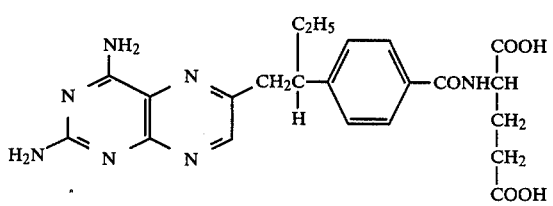

The relationship between N-ethyl-N-deazaminopterin and the N-10 methyl derivative of aminopterin, methotrexate, is apparent from the following:

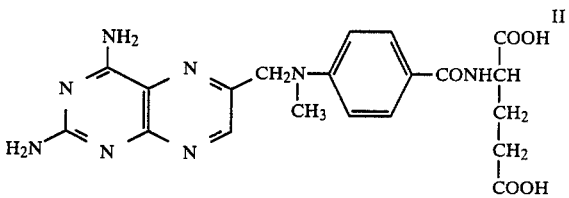

4-Amino-4-deoxy-10-deazapteroic acid, a key intermediate for synthesis of 10-deazaminopterin, was first prepared by DeGraw, Brown, Kisliuk and Gaumont, *Journal of Medicinal Chemistry* 14 866 (1971). DeGraw, Tsakotellis, Kisliuk, and Gaumont, *Journal of Heterocyclic Chemistry* 8 105 (1971) had reported the potent growth -inhibitory activity of 10-deazapteroic acid and its tetrahydro derivative against *Streptococcus faecium*, a folate-dependent organism. Activity was greatly enhanced by reduction to the tetrahydro compound. Accordingly, it was thought that the 2,4-diamino-pteridines should be investigated, because they would be expected to be more capable of cell penetration, and among the 2,4-diamino-pteridines prepared was 4-amino-4-deoxy-10-deazapteroic acid, the compound shown under the Scheme I, Series d, at page 867 of the article.

In the *Journal of Medicinal Chemistry* 17 552 (1974) DeGraw, Kisliuk, Gaumont, Baugh and Nair reported on the synthesis and antifolate activity of 10-deazaminopterin. The antimicrobial and antitumor activities of the powerful dihydrofolic reductase inhibitors aminopterin and its N-10 methyl derivative, methotrexate, are well known, and numerous analogues have been made to further improve the potency, cell penetration and toxicity properties of these compounds. As part of a continuing program, to investigate structure-activity relationships in folic acid analogues, DeGraw et al were interested in the effects of replacement of the nitrogen atom in the side chain of aminopterin, and reported on the synthesis and biological activity of 10-deazaminopterin in this paper. Continuing work with 10-deazaminopterin and its 10-alkyl derivatives has now led to the discovery of their antileukemic activity, and to their efficacy in treating various ascites tumor systems, which are the subject of this invention.

The process of treating leukemia and ascitic tumors according to this invention comprises administering to a warm-blooded animal having an abnormal proportion of leukocytes or other evidences of the malignancy, a therapeutic nontoxic amount of 10-ethyl-10-deazaminopterin as defined above, as such or in the form of a pharmaceutically acceptable salt thereof. These salts are formed with one or more free $NH_2$ groups of the 10-ethyl-10-deazaminopterin.

The process for preparing 10-ethyl-10-deazaminopterin is a synthesis including the following steps, starting from methoxymethyl acetylene (methyl propargyl ether):

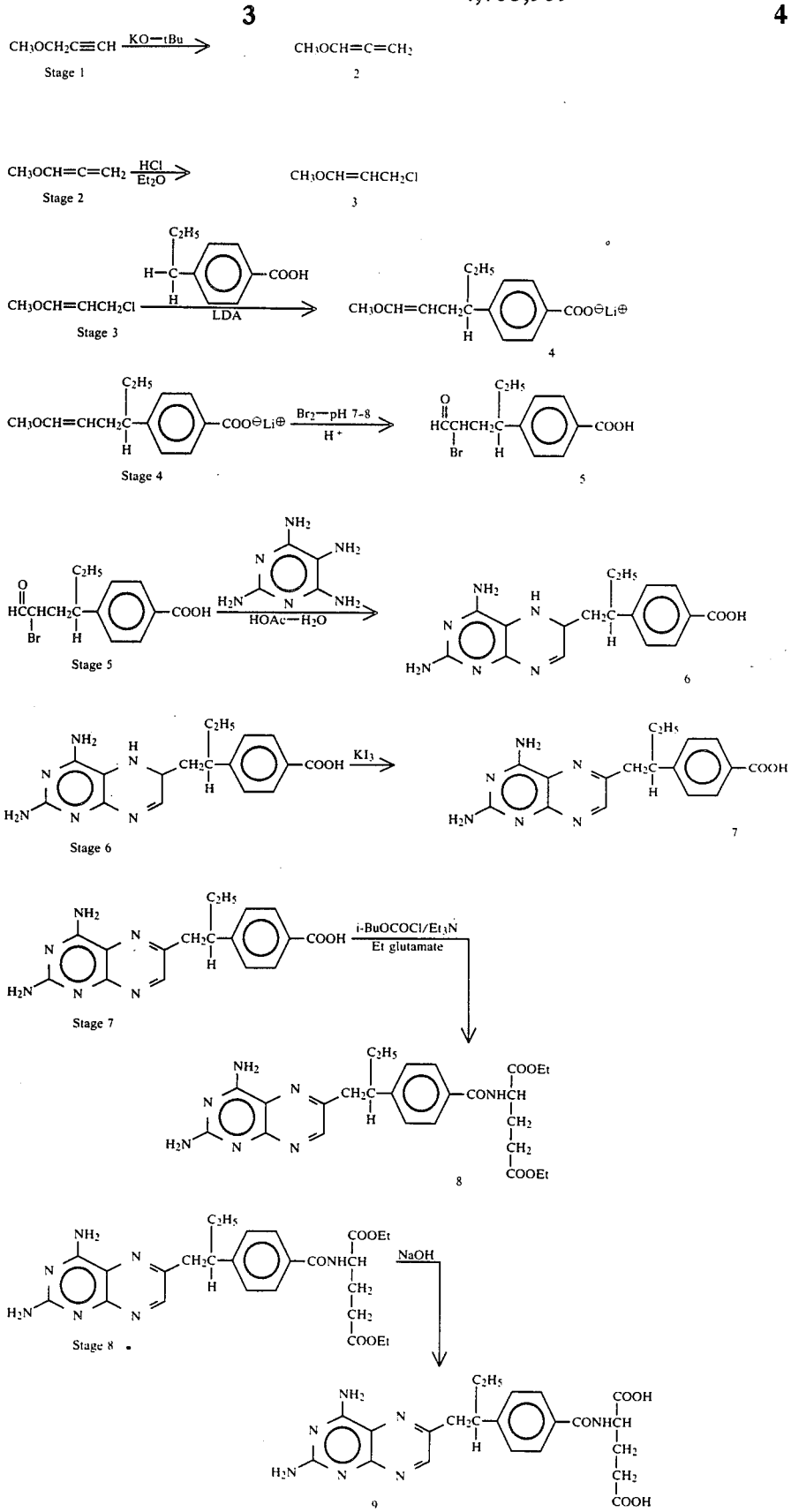
Stage 1 is essentially a rearrangement of methyl propargyl ether to the corresponding 1-methoxy-allene. The rearrangement proceeds under anhydrous conditions, in the presence of alkali, such as, for example, an alkali metal alkoxide, or inorganic alkali or alkali metal with the addition of alcohol. Any lower alkanol such as methyl alcohol, ethyl alcohol, propyl alcohol and butyl alcohol, and the iso, secondary and tertiary isomers thereof can be used as the alkoxide. Sodium and potassium are the preferred alkali metals. The reaction proceeds at elevated temperature, and the use of reflux is a convenient method for controlling temperature. Oxygen should be excluded from the reaction mixture, in order to avoid reaction with the unsaturated groups. An inert atmosphere such as nitrogen can be used.

In Stage 2, hydrogen chloride is added across the allenic double bonds of 1-methoxy-allene. Any alkoxy allene can be used, such as 1-ethoxy-allene. The reaction proceeds under anhydrous conditions, at low temperatures. The addition is made at low temperature, below about −25° C., and desirably below −70° C., to give

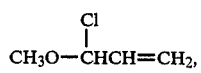

but then the temperature is increased to 0° C. to cause rearrangement to CH$_3$OCH=CHCH$_2$Cl. This reaction also requires exclusion of oxygen, and it can therefore be carried out under an inert atmosphere, such as nitrogen. A solution of anhydrous HCl in an inert solvent such as diethyl ether is added slowly to the 1-methoxy-allene solution in the same solvent. The reaction mixture can be used directly in Stage 3.

In Stage 3, the C10 carbon atom of the benzoic acid group of the 10-deazaminopterin compound is alkylated by the 3-chloro-1-methoxy-propene from Stage 2. The alkylation process requires prereaction of a p-alkylbenzoic acid with a lithium alkylamide catalyst in order to form an active anion reagent. The p-alkyl group has the structure:

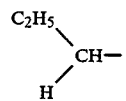

corresponding to the C10 group of the 10-DA with a free hydrogen atom. This process (which also causes ionization of the carboxyl group proton) requires lower temperatures at which it proceeds slowly, for example up to thirty hours. The reaction is preferably carried out under anhydrous conditions under nitrogen in the presence of an inert polar solvent such as tetrahydrofuran. The presence of hexamethylphosphoric triamide (HMPA) cosolvent accelerates the ionization process. After formation of the active anion, the 3-chloro-1-methoxy-propene can then be added slowly to the anion reagent reaction mixture, again at room temperature or below. Since the reactive anion is highly colored, and the reaction product is colorless, the reaction can be followed by discharge of color, and is complete when the reaction mixture is colorless. The solvents can then be removed, and the reaction product worked up.

In Stage 4 of the synthesis, a bromo-acetaldehyde group is formed by bromination and hydrolysis of the methoxy propylene substituent of the Stage 3 reaction product. This reaction proceeds at a pH within the range from about 7 to about 9. Since the aqueous reaction solution from Stage 3 is alkaline, it is carbonated with gaseous carbon dioxide, to reduce the pH to within the range from about 8 to about 9. The reaction may be conducted at a temperature within the range from about 0° to about 50° C., but is preferably conducted at 0° to 5° C.

The reaction proceeds with bromine addition at the ethylene group, and hydrolytic conversion of the bromo methoxide to an aldehyde group, with loss of the HBr. The presence of an inert solvent, such as dichloromethane, facilitates dispersal of the bromine and observation of discharge of bromine color. It is complete when the uptake of bromine reaches the theoretical for the addition of one atom of bromine to the Stage 3 reaction product. From time to time, addition of a buffer such as solid sodium bicarbonate may be required to maintain the pH above 7. The reaction mixture is then acidified by addition of aqueous hydrochloric acid to a pH of about 2. The reaction mixture is worked up by extraction into an organic solvent and removal of solvent, giving the crude bromoacetaldehyde acid reaction product whose formula is given in the synthesis above.

In Stage 5, this reaction product is reacted with 2,4,5,6-tetraaminopyrimidine in aqueous acetic acid, cyclizing the 5,6-amino groups thereof with the aldehyde and bromine groups of the Stage 4 reaction product, and forming a dihydro pteridine ring. The pteridine ring is then dehydrogenated in Stage 6 forming 4-amino-4-desoxy-10-deazaopteroic acid by reaction with potassium iodide/iodine KI$_3$.

The 2,4,5,6-tetraaminopyrimidine sulfate used as the starting material in Stage 5 is first reacted with barium chloride and water to remove the sulfate group, resulting in a barium sulfate precipitate. This can be removed by filtration, and the filtrate can then be used in the Stage 5 reaction.

The Stage 5 cyclization reaction proceeds at an acid pH, preferably within the range from 3 to 5, and consequently an acidic solvent such as aqueous acetic acid can be used. Aqueous acetic acid provides an acidic pH and the organic co-solvent effect of acetic acid aids in solubilizing the bromo aldehydes. The reaction proceeds at moderately elevated temperatures within the range from 35° to 75° C., resulting in the formation of the dihydro pteridine.

This reaction product in the Stage 6 reaction is dehydrogenated with KI$_3$, obtained by dissolving iodine in an aqueous solution of potassium iodide. The KI$_3$ can be added slowly to the dihydro pteridine, and the reaction can be followed by decolorization of the KI$_3$ solution. When decolorization ceases, the reaction is complete. Other suitable oxidizing agents such as hydrogen peroxide or potassium permanganate may be used.

The reaction product is insoluble in the reaction mixture, and separates out. In working up, the material can be filtered, washed and then dried. If desired, the precipitate can be taken up in dilute ammonium hydroxide, and then re-precipitated with dilute acid, such as acetic acid.

The resulting 4-amino-4-desoxy-10-deazapteroic acid is then converted to 10-ethyl-10-deazaminopterin in two steps, Stages 7 and 8. First, the product is reacted with isobutyl chloroformate, and then the diethyl-L-glutamate, converting the pteroic acid group to the corresponding glutamide, diethyl ester, and the esterifying ethyl groups are then hydrolyzed by reaction with dilute aqueous alkali, such as aqueous sodium hydroxide, forming the glutamide free diacid group of 10-ethyl-10-deazaminopterin.

The Stage 7 reaction requires an acid acceptor to take up the liberated hydrogen chloride. The Stage 7 reaction may be conducted with other alkyl chloroformates such as methyl, ethyl, etc. Acid acceptors are preferably organic bases such as tertiary amines or substituted pyridines, for example, triethylamine, tributylamine, N-methylmorpholine, collidine and lutidine. The diethyl glutamate may be added as the free base or as the hydrochloride salt in the presence of an additional equivalent of the acid acceptor.

The reaction proceeds at room temperature or below, preferably 0° to −5° C., and an inert solvent can be used. The isobutyl chloroformate can be added slowly to the reaction mixture, and upon completion of the reaction, diethyl-L-glutamate, organic amine and more solvent can be added, and reaction continued at the same temperature until complete.

The reaction mixture is worked up by removing the solvent by evaporation, preferably in vacuo, and stirring the residue with a mildly alkaline aqueous solution, such as aqueous sodium bicarbonate. The diester is insoluble, and can be recovered by filtration, while unreacted pteroic acid dissolves in the alkaline solution.

Hydrolysis of the esterifying ethyl groups is carried out with aqueous alkali at room temperature or above. The diester can be dissolved in a suitable solvent, such as 2-methoxyethanol, and held in the presence of the aqueous alkali until hydrolysis is complete. The acidic 10-ethyl-10-deazaminopterin is soluble in aqueous alkali, and can then be precipitated by addition of acid, such as glacial acetic acid. The precipitate can be recovered, washed and dried.

The following Examples illustrate application of the synthesis to the preparation of 10-ethyl-10-deazaminopter.

1-Methoxy-allene

The mixture of 100 ml of the methyl propargyl ether (1, dried over 4A sieves) and 3 g of potassium t-butoxide was stirred at reflux for four hours under a very slight flow of nitrogen. The infrared spectrum indicated the rarrangement to be essentially complete. The liquid was distilled through a short path apparatus into a dry ice-cooled receiver to afford 72 g of 1-methoxy-allene; ir 1950 and 850 cm$^{-1}$.

3-Chloro-1-methoxypropene

A stream of dry HCl was passed into 700 ml of anhydrous ether chilled in an ice bath. After 45 g of HCl had been added another 267 ml of fresh ether was added. An aliquot of 541 ml (25.2 g, 0.69 mole HCl) was then added dropwise under nitrogen to a solution of 48.2 g (0.69 mole) of 1 methoxy-allene in 240 ml of ether at −78° C. The addition required 2.5 hours and the internal temperature was kept below −70° C. After thirty minutes the solution was stored in a refrigerator at 0° to 5° C. for twenty-four hours and was used directly in the next step.

4-Amino -4-desoxy-10-ethyl-10-deazapteroic acid

A solution of 192.8 ml (1.38 mole) of freshly distilled diisopropyl amine in 1928 ml of dry THF was chilled to 0° to 5° C. and a solution of 862 ml (1.38 mole) of 1.6M butyl lithium in hexane was added dropwise keeping the temperature around 0° to 5° C. The mixture was stirred another thirty minutes and a solution of 113 g (0.69 mole) of dry p-propyl benzoic acid ($R_1=H$, $R_2=C_2H_3$) in 385 ml of dry THF was added dropwise at 0° to 5° C. The red mixture was stirred at this temperature for 3.5 hours and then kept at 0° to 5° C. in a cold room for twenty-five hours. The ether solution of 3-chloro-1-methoxypropene above was then added dropwise over 1.5 hour at 0° to 5° C.; quenching the red color was completed at the end of the addition period. After two hours the solvents were removed in vacuo and the residue partitioned between 1 liter of water and 1 liter of ether. The aqueous portion was chilled, treated with gaseous $CO_2$ until it was pH 8 to 9, and 240 ml of $CH_2Cl_2$ was added. Then, at 0° to 5° C. was added, dropwise with stirring, 1MBr$_2$ in $CH_2Cl_2$ until persistence of the red color (85% uptake of Br$_2$ observed). Solid NaHCO$_3$ was occasionally added to keep the pH at 7 to 8. The mixture was acidified to pH~2 with 6N HCl (~50 ml). The $CH_2Cl_2$ layer was removed and the aqueous extracted with another 200 ml of $CH_2Cl_2$. The combined organic extracts were dried over MgSO$_4$ and evaporated in vacuo to leave an orange syrupy residue of the crude bromoaldehyde acid.

A mixture of 156.2 g (0.66 mole) of 2,4,5,6-tetraamino pyrimidine sulfate (Aldrich), 160.3 g (0.65 mole) of BaCl$_2$.2H$_2$O and 3 liters of water was stirred at room temperature for 1.5 hours. The mixture was warmed to 70° C., filtered hot and the filtrate cooled to room temperature. The filtrate was adjusted to pH 3 to 4 with 10% NaOH, warmed to 45° C. and treated over ten minutes with the bromoaldehyde above in 1075 ml of glacial HOAc. The mixture was stirred at 50° for 1.5 hours, decanted to remove some insoluble gum and cooled to room temperature. The solution containing the dihydro pteridine was treated dropwise with aqueous KI$_3$ (from 81.9 g I$_2$-156.2 g KI-1075 ml H$_2$O) until decolorization of the KI$_3$. The solution was allowed to stand for twenty-four hours and the yellow precipitate collected, washed with water and ethanol and dried. The material was stirred with 1800 ml of H$_2$O containing 20 ml of concentrated NH$_4$OH for two hours and filtered. The filtrate was acidified with HOAc to precipitate the product, which was collected, washed with water and dried, to afford a 32% yield, which analyzed as follows after crystallization from methanol:

| Formula (MW) | Analyzed Calculated | Analyzed Found | 0.1 N—HCl λ max. NM(E) | 0.1 N—NaOH λ max. NM(E) |
|---|---|---|---|---|
| $C_{17}H_{18}N_6O_2$ 2/5 $CH_3OH$ (351.178) | C 59.51 H 5.62 N 23.93 | C 59.83 H 5.39 N 23.62 | 242 (22,622) 338 (6,568) | 255 (26,281) 370 (6,398) |

10-Ethyl-10-deazaminopterin

The mixture of 19.6 g (0.058 mole) of the pteroic acid, 15.8 ml of triethylamine (0.116 mole) and 900 ml of dry DMF was warmed to 80° C. with stirring until nearly complete solution was obtained. The solution was cooled to 0° to 5° C. in an ice bath and treated dropwise with 15.0 ml of isobutyl chloroformate (0.116 mole). After 1.5 hour at 0° to 5° C. the mixture was treated with a mixture of 28.0 g (0.116 mole) of diethyl-L-glutamate hydrochloride, 15.8 ml of triethylamine (0.116 mole) and 100 ml of dry DMF. The mixture was stirred for two hours in the ice bath and at room temperature for twenty-four hours.

Dimethylformamide was evaporated under reduced pressure (~1 mm) and the residue was stirred with 400 ml 5% NaHCO$_3$ and 400 ml of ether for one hour. The mixture was filtered and the cake washed with water and ether and dried to leave the diester.

The diester was dissolved in 200 ml of 2-methoxy ethanol and treated with 100 ml of 1N NaOH. The solution was kept at room temperature for 4.5 hours and then diluted with 1 liter of $H_2O$. The solution was acidified with glacial HOAc until precipitation was complete. The precipitate was collected by filtration. The cake was resuspended in water with stirring, filtered and dried to leave crude 10-ethyl-10-deazaminopterin; HPLC indicated 90% 10-ethyl-10-deazaminopterin and 10% of the unreacted pteroic acid. The yield was 30%.

After purification by preparative HPLC the product analyzed as follows:

| Formula (MW) | Analyzed | | 0.1 N—HCl λ max. NM(E) | 0.1 N—NaOH λ max. NM(E) |
|---|---|---|---|---|
| | Calculated | Found | | |
| $C_{22}H_{25}N_7O_5$ | C 52.95 | C 53.43 | 242 (29,134) | 255 (30,731) |
| 7/4 $H_2O$ | H 5.41 | H 5.43 | | |
| (494.515) | N 19.63 | N 19.23 | 338 (10,102) | 370 (7,582) |

The 10-ethyl-10-deazaminopterin can be administered per se, or in association with a pharmaceutically acceptable diluent or carrier. The invention accordingly also provides a pharmaceutical composition in dosage unit form comprising from 0.1 to about 500 mg of 10-ethyl-10-deazaminopterin, per dosage unit, together with a pharmaceutically acceptable nontoxic inert carrier or diluent therefor.

The 10-ethyl-10-deazaminopterin can be used as such, or in the form of an acid addition salt. These salts are formed with one or more free $NH_2$ groups of the 10-deazaminopterin molecule.

The acid addition salts are preferably the pharmaceutically acceptable, nontoxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicylic, o-acetyloxybenzoic, nicotinic and isonicotinic acid, and organic sulphonic acids, for example, methanesulphonic, ethanesulphonic, 2-hydroxyethanesulphonic, toluene-p-sulphonic, and naphthalene-2-sulphonic acid. An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

The 10-ethyl-10-deazaminopterin or salt thereof can be administered to the animal by any available route, including oral and parenteral (intravenous, intraperitoneal, subcutaneous, and intramuscular administration. The amount administered is sufficient to ameliorate the leukemia or the ascitic tumor, and will depend upon the type of leukemia, the species of animal, and the weight of the animal. For example, in human administration, a dosage of 10-deazaminopterin compound in within the range from about 0.1 mg/kg to about 500 mg/kg per day should be sufficient. Dosages in the higher part of the range, approaching 500 mg/kg, are normally administered in conjunction with leucovoran (dl-5-formyl tetrahydrofolate) to reduce toxicity. In the treatment of lower test animals, a similar dosage range is therapeutic. The upper limit of dosage is that imposed by toxic side effects, and can be determined by trial and error for the animal to be treated, including humans.

To facilitate administration, the 10-ethyl-10-deazaminopterin or salt thereof can be provided in composition form, and preferably in dosage unit form. While the compound can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the 10-ethyl-10-deazaminopterin. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl- and propyl-hydroxybenzoate, talc or magnesium stearate.

For convenience in handling, the 10-ethyl-10-deazaminopterin and carrier or diluent can be enclosed or encapsulated in a capsule, sachet, cachet, gelatin, paper or other container, especially when intended for use in dosage units. The dosage units can for example take the form of tablets, capsules, suppositories or cachets.

The following Examples illustrate various forms of dosage units in which the 10-ethyl-10-deazaminopterin or salts thereof can be prepared:

EXAMPLE 1

| Tablet formulation | |
|---|---|
| | Mg/tablet |
| 10-Ethyl-10-Deazaminopterin | 15 |
| Lactose | 86 |
| Corn starch (dried) | 45.5 |
| Gelatin | 2.5 |
| Magnesium stearate | 1.0 |

The 10-ethyl-10-deazaminopterin is powdered and passed through a mesh sieve and well mixed with the lactose and 30 mg of the corn starch, both passed through a sieve.

The mixed powders are massed with a warm gelatin solution, prepared by stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE 2

| Tablet formulation | |
|---|---|
| | Mg/tablet |
| 10-Ethyl-10-Deazaminopterin | 100 |
| Lactose | 39 |
| Corn starch (dried) | 80 |
| Gelatin | 4.0 |
| Magnesium stearate | 2.0 |

The method of preparation is identical with that of Example 1 except that 60 mg of starch is used in the granulation process and 20 mg during tabletting.

EXAMPLE 3

| Capsule formulation | |
|---|---|
| | Mg/capsule |
| 10-Ethyl-10-Deazaminopterin | 250 |
| Lactose | 150 |

The 10-ethyl-10-deazaminopterin and lactose are passed through a sieve and the powders well mixed together before filling into hard gelatin capsules of suitable size, so that each capsule contains 400 mg of mixed powders.

EXAMPLE 4

| Suppositories | |
|---|---|
| | Mg/suppositories |
| 10-Ethyl-10-Deazaminopterin | 50 |
| Oil of Theobroma | 950 |

The 10-ethyl-10-deazaminopterin is powdered and passed through a sieve and triturated with molten oil of theobroma at 45° C. to form a smooth suspension.

The mixture is well stirred and poured into molds, each of nominal 1 g capacity, to produce suppositories.

EXAMPLE 5

| Cachets | |
|---|---|
| | Mg/cachet |
| 10-Ethyl-10-Deazaminopterin | 100 |
| Lactose | 400 |

The 10-ethyl-10-deazaminopterin is passed through a mesh sieve, mixed with lactose previously sieved and fitted into cachets of suitable size so that each contains 500 mg.

EXAMPLE 6

| Intramuscular injection (sterile suspension in aqueous vehicle) | |
|---|---|
| | Mg |
| 10-Ethyl-10-Deazaminopterin | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE 7

| Intraperitoneal intraveneous or subcutaneous injection (sterile solution in aqueous carrier system) | |
|---|---|
| | Mg |
| 10-Ethyl-10-Deazaminopterin, hydrochloric acid addition salt | 15 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

The following Example illustrates administration of 10-ethyl-10-deazaminopterin using a standardized test procedure:

EXAMPLE 8

Sodium hydroxide (0.2 ml of 0.1N) was added to 5 mg of 10-ethyl-10-deazaminopterin. Distilled water was then added, the pH adjusted to 7.0, and the solution then diluted with distilled water to 10 ml.

The resulting solution and dilutions thereof were administered in aliquots of 0.1 ml by intraperitoneal injection into L1210 leukemic BD (2) $F_1$ female mice (A. R. Schmid, Madison, Wis.). Injections were given once per day, three times per week (Monday, Wednesday, Friday) starting one day after tumor transplantation ($10^6$ cells/mouse). Therapy was continued until death of the animals.

For comparison purposes, and as a control, a parallel series of tests was carried out simultaneously using L1210 leukemic BD (2) $F_1$ female mice, under exactly the same test conditions, administering methotrexate instead of 10-ethyl-10-deazaminopterin.

The procedure for testing, and the maintenance and transplantation of the L1210 leukemia, is in accordance with the method of Hutchinson, D. J., Robinson, D. C., Martin, D., Ittensohn, O. L. and Dillenberg, *Journal Cancer Res.* 22 57–72 (1962). The antileukemic activity of 10-ethyl-10-deazaminopterin was evaluated against methotrexate in terms of the increase in median life span obtained at various dosages, up to the maximum tolerated level, when compared to untreated controls. Toxicity of various dosages was evaluated by the extent of weight loss and eventual death, with no evidence of tumor.

Representative results obtained against the L1210 leukemia are as follows:

TABLE

L1210 Leukemia:
Inoculum: $10^6$ cells
Host: BD (2) $F_1$ female mice
Vehicle: Buffered isosaline
Schedule: Every two days times five

| Mice (Exp's × No.) | Dosage (mg/kg) | Methotrexate AST days | Methotrexate ILS % | 10-ethyl-10-deazaminopterin AST days | 10-ethyl-10-deazaminopterin ILS % |
|---|---|---|---|---|---|
| 5 × 2 | — | 6.7 ± 0.7 | — | 6.7 ± 0.7 | — |
| 5 × 2 | 6 | 13.8 ± 1.2 | +105 | | |
| 5 × 2 | 9 | 15.8 ± 1.7 | +135 | | |
| 5 × 2 | 12 | 16.9 ± 1.5 | +149 | 18.3 ± 1.7 | +172 |
| 5 × 2 | 18 | 17.3 ± 1.8 | +158 | 21.8 ± 1.4 | +220 |
| 5 × 2 | 24 | 15.3 ± 2.1 | +127 | | |

It is apparent from the above results that the life span of the test mice was very considerably increased by administration of 10-ethyl-10-deazaminopterin. Increased dosages led to increased life spans, the maximum life span being obtained with the maximum dose, about 22 mg/kg, at which dosage level a slight toxicity was observed, as evidenced by a decrease in weight change. The results show 10-ethyl-10-deazaminopterin on a similar dosage level to be superior to methotrexate, and since methotrexate is accepted as effective, 10-ethyl-10 deazaminopterin is to be expected to be at least as effective as methotrexate under similar conditions, and probably slightly more powerful, dosagewise. The potent antileukemic activity of 10-ethyl-10-deazaminopterin is evident from these test results.

Having regard to the foregoing disclosure, the following is claimed as inventive and patentable embodiments thereof:

1. A pharamceutical composition in tablet form for treating leukemia or an ascites tumor comprising an amount within the range from about 0.1 to about 500 mg of 10-ethyl-10-deazaminopterin per tablet therapeutically effective to ameliorate leukemia or the ascites tumor, together with a pharmaceutically acceptable nontoxic carrier or diluent therefor.

2. A pharmaceutical composition according to claim 1 in which the 10-ethyl-10-deazaminopterin is in the form of a pharmaceutically acceptable acid addition salt or quaternary ammonium derivative.

3. A pharmaceutical composition in capsule form for treating leukemia or an ascites tumor comprising an amount within the range from 0.1 to about 500 mg of 10-ethyl-10-deazaminopterin per capsule therapeutically effective to ameliorate leukemia or the ascites tumor, together with a pharmaceutically acceptable nontoxic inert carrier or diluent therefor.

4. A pharmaceutical composition according to claim 3 in which the 10-ethyl-10-deazaminopterin is in the form of a pharmaceutically acceptable acid addition salt or quaternary ammonium derivative.

5. A pharmaceutical composition in suppository form for treating leukemia or an ascites tumor comprising an amount within the range from about 0.1 to about 500 mg of 10-ethyl-10-deazaminopterin per suppository therapeutically effective to ameliorate leukemia or the ascites tumor, together with a pharmaceutically acceptable nontoxic inert carrier or diluent therefor.

6. A pharmaceutical composition according to claim 5 in which the 10-ethyl-10-deazaminopterin is in the form of a pharmaceutically acceptable acid addition salt or quaternary ammonium derivative.

7. A pharmaceutical composition in cachet form for treating leukemia or an ascites tumor comprising an amount within the range from about 0.1 to about 500 mg of a 10-ethyl-10-deazaminopterin per cachet therapeutically effective to ameliorate leukemia or the ascites tumor, together with a pharmaceutically acceptable nontoxic inert carrier or diluent therefor.

8. A pharmaceutical composition according to claim 7 in which the 10-ethyl-10-deazaminopterin is in the form of a pharmaceutically acceptable acid addition salt or quaternary ammonium derivative.

9. A pharmaceutical composition in sterile aqueous form for treating leukemia or an ascites tumor comprising an amount within the range from about 0.1 to about 500 mg of 10-ethyl-10-deazaminopterin therapeutically effective to ameliorate leukemia or the ascites tumor, together with a pharmaceutically acceptable nontoxic sterile inert aqueous carrier or diluent therefor.

10. A pharmaceutical composition according to claim 9 in which the 10-ethyl-10-deazaminopterin is in the form of a pharmaceutically acceptable acid addition salt or quaternary ammonium derivative.

11. A pharmaceutical composition according to claim 9 in aqueous solution form.

12. A pharmaceutical composition according to claim 9 in aqueous dispersion form.

13. A proeess for treating leukemia and ascites tumors which comprises administering to a warm-blooded animal having an abnormal proportion of leukocytes or other evidence of the malignancy, a therapeutic and relatively nontoxic amount of 10-ethyl-10-deazaminopterin.

14. A process according to claim 13 in which the 10-ethyl-10-deazaminopterin is administered as a pharmaceutically acceptable salt thereof.

15. A process according to claim 13 in which the 10-ethyl-10-deazaminopterin is administered in an amount within the range from about 0.1 to about 500 mg per day.

16. A process according to claim 13 in which the 10-ethyl-10-deazaminopterin is administered with an inert diluent or carrier.

17. A process according to claim 13 in which the 10-ethyl-10-deazaminopterin is administered orally.

18. A process according to claim 13 in which the 10-ethyl-10-deazaminopterin is administered parenterally.

* * * * *